United States Patent
Alff et al.

(10) Patent No.: US 10,795,806 B2
(45) Date of Patent: Oct. 6, 2020

(54) DEVICES AND METHODS FOR GENERATING A STREAM OF HEALTH-RELATED DATA

(71) Applicant: VOLUNTIS, S.A., Paris (FR)

(72) Inventors: Patrick Alff, Suresnes (FR); Laurent Wiart, Prigonrieux (FR); Etienne Vial, Poissy (FR)

(73) Assignee: VOLUNTIS S.A., Paris (FR)

( * ) Notice: Subject to any disclaimer, the term of this patent is extended or adjusted under 35 U.S.C. 154(b) by 0 days.

(21) Appl. No.: 16/296,323

(22) Filed: Mar. 8, 2019

(65) Prior Publication Data
US 2020/0285568 A1  Sep. 10, 2020

(51) Int. Cl.
| | | |
|---|---|---|
| *G06F 9/44* | (2018.01) | |
| *G06F 11/36* | (2006.01) | |
| *G06F 9/445* | (2018.01) | |
| *G06F 8/34* | (2018.01) | |
| *G06F 8/20* | (2018.01) | |

(52) U.S. Cl.
CPC .......... *G06F 11/3684* (2013.01); *G06F 8/20* (2013.01); *G06F 11/3664* (2013.01); *G06F 11/3688* (2013.01); *G06F 11/3692* (2013.01)

(58) Field of Classification Search
CPC .......... G06F 11/3684; G06F 8/34; G06F 8/20; G06F 8/30; G06F 8/10; G06F 8/65; G06F 8/35; G06F 11/3688; G06F 11/3664; G06F 11/3692; G06F 11/3672; G06F 11/3676; G06N 20/00; H04L 67/10; H04L 67/02
See application file for complete search history.

(56) References Cited

U.S. PATENT DOCUMENTS

| | | | |
|---|---|---|---|
| 6,188,976 B1 | 2/2001 | Ramaswamy et al. | |
| 7,155,705 B1 | 12/2006 | Hershberg et al. | |
| 8,464,204 B1 | 6/2013 | Thornton et al. | |
| 9,032,361 B2* | 5/2015 | Dhalait | G06F 11/3684 717/104 |
| 9,898,396 B2* | 2/2018 | Owen | G06F 11/3688 |
| 10,078,501 B2* | 9/2018 | Narayanan | G06F 8/35 |

(Continued)

OTHER PUBLICATIONS

Bernardino et al., Canopus: A Domain-Specific Language for Modeling Performance Testing, 11 pages (Year: 2016).*

(Continued)

*Primary Examiner* — Thuy Dao
(74) *Attorney, Agent, or Firm* — Tutunjian & Bitetto, P.C.

(57) ABSTRACT

A method and device for generating a stream of data that is representative of at least an algorithm (44) of a software as a medical device. To reach that aim, the method comprises designing (41) the at least an algorithm using first programming language items of a determined domain-specific language (DSL), which is obtained using a determined language workbench (LWB) environment. The method further comprises simulating (42) an executing of the at least an algorithm with a simulation environment obtained using second programming language items of the determined DSL, the simulating being implemented in the determined LWB environment; testing (43) the at least an algorithm with at least a test function written with third programming language items of the DSL, the testing being implemented in the determined LWB environment; and generating (440) the stream of data.

12 Claims, 6 Drawing Sheets

(56) References Cited

U.S. PATENT DOCUMENTS

| | | | |
|---|---|---|---|
| 10,339,036 B2* | 7/2019 | Dwarakanath | G06F 11/3684 |
| 10,387,124 B2* | 8/2019 | Chaudhuri | G06F 8/35 |
| 2002/0059404 A1 | 5/2002 | Schaaf et al. | |
| 2003/0233343 A1 | 12/2003 | Li | |
| 2004/0068504 A1 | 4/2004 | Gobbi et al. | |
| 2004/0139095 A1 | 7/2004 | Trastour et al. | |
| 2004/0163091 A1 | 8/2004 | Brill | |
| 2005/0097453 A1 | 5/2005 | Simonyi | |
| 2005/0188347 A1 | 8/2005 | Dorn et al. | |
| 2007/0006153 A1 | 1/2007 | Sultan | |
| 2008/0189689 A1 | 8/2008 | Tramontana et al. | |
| 2008/0288856 A1 | 11/2008 | Goranson et al. | |
| 2009/0288068 A1 | 11/2009 | Gunsel et al. | |
| 2017/0286070 A1* | 10/2017 | Holzleitner | G06F 8/35 |

OTHER PUBLICATIONS

M. Voelter et al., Using Language Workbenches and Domain-Specific Languages for Safety-Critical Software Development, Software & Systems Modeling, May 17, 2018, pp. 1-24, Springer Berlin Heidelberg.

M. Voelter et al., Languages, Generators Runtimes Testing andfor a Safety-Critical System, Voelter Presentation, May 17, 2018, pp. 1-35.

M. Voelter et al., Using Language Workbenches and Domain-Specific Languages for Safety-Critical Software Development, Voelter Presentation, May 17, 2018, pp. 1-34.

* cited by examiner

DEVICES AND METHODS FOR GENERATING A STREAM OF HEALTH-RELATED DATA

1. TECHNICAL FIELD

The present document relates to the domain of health-related device application(s) (also called health Apps) and designing of such health-related device application(s). The present document also relates to the design of computer algorithm(s) for the management of medical conditions in telehealth and/or medical devices. The present document is also understood in the context of the designing and implementing of software as medical device.

2. BACKGROUND

This section is intended to introduce the reader to various aspects of art, which may be related to various aspects that are described and/or claimed below. This discussion is believed to be helpful in providing the reader with background information to facilitate a better understanding of the present description. Accordingly, these statements are to be read in this light, and not as admissions of prior art.

With the development of the Internet and of technologies to access the Internet from everywhere, new tools and new ways of consuming the information have appeared with time. For example, in the domain of healthcare, individuals and healthcare experts have been proposed new tools under the form of mobile applications and/or medical devices to, e.g., help them in establishing a diagnosis or make clinical decisions.

Among these new tools, one may cite the Software(s) as Medical Devices (SaMD), which correspond to software(s) being used in healthcare and created for medical purposes for example. Definition and key concepts of SaMD are provided by IMDRF (International Medical Device Regulator Forum) in a document entitled "Software as a Medical Device (SaMD): Key Definitions" by the IMDRF SaMD Working Group and published on Dec. 9, 2013.

The development of SaMDs is usually done by creating the software for each target architecture:
- For Apple iOS® devices: development in Objective C and/or Swift;
- For Google Android® devices: development in Java and/or Kotlin;
- For Web application: development in one of the many available languages/frameworks, for example C#/.NET, PHP/Zend, NodeJS, Java/Sprng/JSFIGWT.

Each component of the SaMD (also called software hereinafter) must then be developed by several software experts for the various target environments in which the software must operate. As a result, an example application targeting iOS® and Android® mobile devices may be developed twice by different software experts. Apart from doubling the effort, the risk for different understandings/implementations of the software is very likely, that could lead to different application behaviors or bugs on different architectures. Some recent cross-platform frameworks have been created to allow the development software for all mobile architectures at once, e.g. Xamarin, React Native, Ionic, etc. But those frameworks usually target mobile architectures, thus not mitigating the issue for web applications and require the software experts to learn about a new API (Application Program Interface) than those they are already accustomed to when developing for Apple iOS® or Google Android®.

The development of such software is usually done with GPL (General Purpose Languages), such as C#, Java, PHP, etc. Such a GPL is the domain of software experts and reading the programming code of GPL is not an option for other domain experts such as HCP (Health-Care Professional), who may oversee checking the reliability of the software regarding the (functional) specification. As a result, HCPs who provide medical insight on the goals and behavior of the software cannot provide input at the code level to ensure the software written is behaving as they expect. They then must wait for the software to be readily executable/usable on target devices to ensure it behaves as expected from a medical standpoint.

As a corollary of the difficulty in checking the programming code, delays can be long between the ideation/specification phase and the realization phase of the software. It might easily take several months for the software experts to implement the software, slowing down the whole iterative process of developing the software (specification, implementation, review and feedback, update of the specification, software modifications and reimplementation).

Finally, the development of the software with a GPL can be performed in such ways that the medical logic (the "core" of the medical application) is hard to separate from the overall logic of the application (data management, display, exception handling, etc.), making it hard to clearly identify which parts are related to the specific medical logic from the parts for "house-keeping" logic. This point makes the testing of software for each target architecture hard as well. Also, the degrees of freedom in design and architecture of software provided by GPL allow to develop medical algorithms in "as many ways as there are software specialists", which can lead to good architecture/design, as well as bad (not scalable, hard to maintain, bug-prone).

3. SUMMARY

References in the specification to "one embodiment", "an embodiment", "an example embodiment", "a particular embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

According to one embodiment, a method of generating a stream of data, the data being representative of at least an algorithm of a software as a medical device, the method comprising:
- designing the at least an algorithm using first programming language items of a determined domain-specific language, the determined domain-specific language being obtained using a determined language workbench environment;
- simulating an executing of the at least an algorithm with a simulation environment obtained using second programming language items of the determined domain-specific language, the simulating being implemented in the determined language workbench environment;
- testing the at least an algorithm with at least a test function written with third programming language items of the determined domain-specific language, the testing being implemented in the determined language workbench environment;

generating the stream of data.

According to a variant, the at least an algorithm is designed according to a model of a finite state automaton.

According to another variant, the method further comprises automatically generating a graphical representation of at least a medical protocol from the at least an algorithm in the determined language workbench environment.

According to an additional variant, the method further comprises interpreting and processing the stream of data in a run-time environment embedded in at least a target application.

According to a further variant, the at least a target application is configured to be executed on a determined target architecture among a plurality of target architectures, the run-time environment being identical for any target architecture of the plurality.

According to another embodiment, a device configured for generating a stream of data, the data being representative of at least an algorithm of a software as a medical device, the device comprising a memory associated with at least a processor configured for:

designing the at least an algorithm using first programming language items of a determined domain-specific language, the determined domain-specific language being obtained using a determined language workbench environment;

simulating an executing of the at least an algorithm with a simulation environment obtained using second programming language items of the determined domain-specific language, the simulating being implemented in the determined language workbench environment;

testing the at least an algorithm with at least a test function written with third programming language items of the determined domain-specific language, the testing being implemented in the determined language workbench environment;

generating the stream of data.

According to a further embodiment, a system comprising the abovementioned device configured for generating a stream of data and an apparatus comprising a memory associated with at least a processor configured for interpreting and processing the stream of data in a run-time environment embedded in at least a target application.

According to another embodiment, a signal carrying on a stream of data representative of at least an algorithm of a software as a medical device, said stream of data being generated according to the abovementioned method.

According to a further embodiment, a computer program product comprises program code instructions to execute the steps of the method(s), when this program is executed on a computer.

According to another embodiment, a (e.g., non-transitory) processor readable medium has stored therein instructions for causing a processor to perform the steps of the method(s).

4. LIST OF FIGURES

The present specification will be better understood, and other specific features and advantages will emerge upon reading the following description, the description making reference to the annexed drawings wherein.

5. DETAILED DESCRIPTION OF EMBODIMENTS

The subject matter is now described with reference to the drawings, wherein like reference numerals are used to refer to like elements throughout. In the following description, for purposes of explanation, numerous specific details are set forth in order to provide a thorough understanding of the subject matter. It can be evident, however, that subject matter embodiments can be practiced without these specific details.

According to non-restrictive embodiments, methods and devices to generate, transmit and/or receive data representative of one or more medical algorithm are disclosed. It will be appreciated that those skilled in the art will be able to devise various arrangements from the embodiments described hereinbelow.

One or more embodiments of a method for (and an apparatus configured for) generating and/or outputting a stream of data that is representative of one or more algorithm of a Software as Medical Device (SaMD). To reach that aim, the one or more algorithms are designed using first programming language items of a determined Domain-Specific Language (DSL), i.e. a DSL specific to healthcare domain. A programming language item may also be called a language concept. The DSL may be obtained (i.e. defined and/or generated) by using a determined Language Work-Bench (LWB) environment, for example MPS (Meta Programming System) developed by Jetbrains, Xtext or Kermeta. The execution of the one or more algorithms may be simulated in the same determined LWB environment, with a simulation environment that may be obtained with second programming language items of the same determined DSL than the one used to design the one or more algorithms. The one or more algorithms may further be tested in the same determined by using test function(s) and/or testing scenario(s) written with third programming language items of the same determined DSL than the one used to design and simulate the one or more algorithms.

The first, second and third programming language items may each form a subset of a set of programming language items/concepts forming the DSL.

The use of a DSL specifically targeted to the design/test/simulation of medical algorithms enables the use of a small set of "commands" or concepts for the medical field in comparison to GPL for example, more easily learnable and providing a simpler common understanding of the medical algorithms, even for non-software experts, i.e. for HCP for example. Moreover, the use of a same LWB environment for the design/test/simulation of the one or more algorithms enable to speed up the whole process of developing the SaMD by easing the interactions between the design module, the test module and the simulation module of the environment used to develop the one or more algorithms of the SaMD.

A DSL (Domain Specific Language) is a programming language especially targeted to a specific domain (finance, aeronautics, taxes, aerospace, medical, etc.). DSLs are computer languages optimized for expressing programs in a particular domain. They may have different degrees of expressivity—from simple structure languages to Turing complete languages—and use a wide variety of notations such as text, tables, symbols, math, diagrams. Importantly, the abstractions and notations used in the DSL are aligned with the particular domain at which the DSL is targeted; this is the core difference to general-purpose programming languages, whose abstractions are generic. Many DSLs are used by people who are competent in the domain, but who are not necessarily developers. For those DSLs, notations that reflect the domain are especially important, even if those might not resemble popular syntax from general purpose languages.

The DSL according to this document is targeted to writing medical algorithms to, for example, follow and manage side effects of therapeutic treatments (e.g. oncology, diabete), or provide an assistance in establishing a diagnosis according to symptoms (fever, diarrhea). Instead of writing those algorithms in General Purpose Languages such as Java, C, C#, the DSL is targeted to a determined use: commands to send messages (prompts, medical recommendations), ask for inputs (temperature, list of symptoms a patient might experience with yes/no answers, etc.).

Examples of items/concepts (e.g., important parameters and actions for a medical algorithm: configuration parameters, outputs, messages, questionnaires, custom events in (inputs to the medical algorithm), events out (outputs from the medical algo), notifications) of the determined DSL are as follows:

state machine DiarrheaStateMachine
   configuration parameters:
   diarrheaInputNumberOfStoolsBaseline:
opt<DiarrheaBaseline>
   diarrheaInputHasOstomy: boolean
   diarrheaInputImmunoOncologyTreatment: boolean
   diarrheaInputSelectEpisodeDuration: DiarrheaEpisodeDuration
   diarrheaInputGrade1RecoSelect:
DiarrheaGradeReco1Select
   diarrheaInputGrade2RecoSelect:
DiarrheaGradeReco2Select
   diarrheaInputLevel2SymptomsRecoDecisionIsCall:
Boolean
   diarrheaInputLastRecoCallThenCallAgain: boolean
   outputs:
   messages:
   MessageAppContent(message:DiarrheaEventLabels, diarrheaBaseline:DiarrheaBaseline, numberOfStoolsOver24 Hour
   MessageAppConfirmation(message:DiarrheaConfirmMessage, numberOfStoolsOver24 hr:DiarrheaStools, ostomyOutput: DiarrheaUSostomyOutput, looseOrWatery:DiarrheaAdditionalConfirmationEnums, symptomsIntro:DiarrheaAdditionalConfirmationEnums, diarrheaSymptoms:string, diarrheaTakingAntiDiarrheaMedication:DiarrheaAdditionalConfirmationEnums)
   MessageAppRecommendation(message:DiarrheaUSReco, symptomString:DiarrheaUSReco)
   questionnaires:
   custom events in: eventInAskDiarrheaNumberOfStools (numberOfStoolsQuestionnaire:DiarrheaNumbe rOfStoolsQuestionnaire) medical
   eventInAskDiarrheaNumberOfStoolsFirst(numberOfStoolsFirstQuestionnaire: DiarrheaNumberOfStoolsFirstQuestion) medically relevant
   eventInAskDiarrheaOstomyOutput(ostomyOutputQuestionnaire:DiarrheaOsto myOutputQuestionnaire) medically rele
   eventInAskDiarrheaAssociatedSymptomsLevel1(associatedSymptomsLevel1 Questionnaire:DiarrheaAssociatedSymptom) medically relevant
   eventInAskDiarrheaAssociatedSymptomsLevel2(associatedSymptomsLevel2 Questionnaire:DiarrheaAssociatedSymptom) medically relevant
   eventInAskDiarrheaAntiDiarrheaMedication(antiDiarrheaMedicationQuestionn aire:DiarrheaAntiDiarrheaMedicatio) medically relevant
   eventInAskDiarrheaLooseOrWateryBowelMovements (looseOrWateryQuestion nair) medically relevant
   eventInAskConfirmation(confirmation:boolean) medically not relevant
   eventInAskCancel( ) medically not relevant
   eventInAskBack( ) medically not relevant
   eventInAskReInitialize( ) medically not relevant
   events out:
   eventOutSendRecoRecord(recoRecord:DiarrheaRecoRecord) medically relevant
   eventOutSendEpisodeRecord(earrheaEpisodeRecord) medically relevant
   eventOutSendRecoExplanationRecord(recoExplanationRecord:DiarrheaReco ExplanationRecord) medically relevant
   eventOutNonCompliance( ) medically relevant
   notifications: NotificationUpdateDiarrhea(message:DiarrheaUSUserRequest)

A LWB (language workbench) is a tool that efficiently supports the development of languages, for example DSLs; the report from the language workbench challenge provides a good overview. They typically provide a set of DSLs to define various aspects of languages, such as structure, syntax, static semantics, dynamic semantics (usually through interpreters or generators) as well as various aspects relating to Integrated Development Environments (IDEs) (code completion, syntax coloring, goto definition, find usages, refactorings).

Non-limiting examples of LWB environments are Jetbrains MPS, Xtext, Kermeta.

Figure 1:
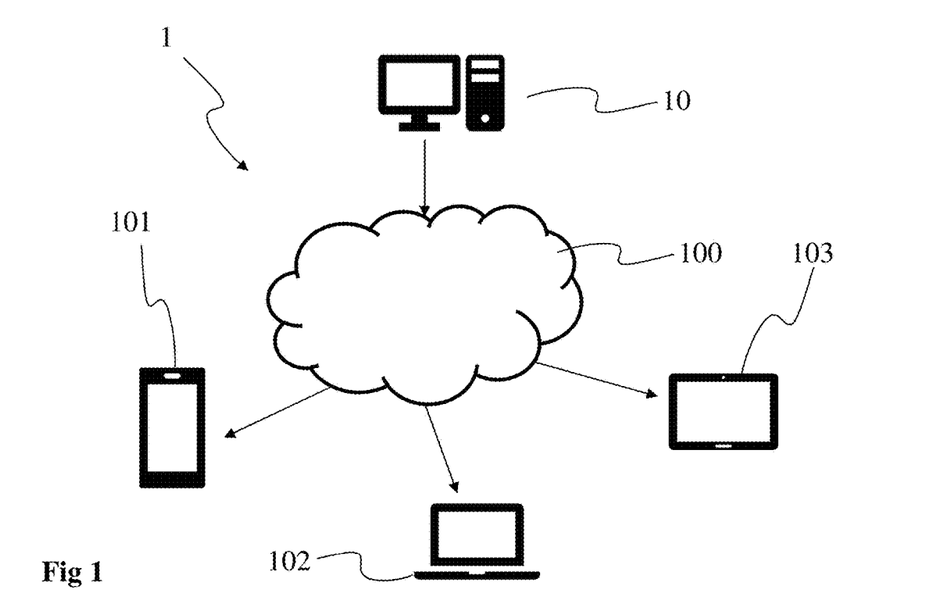
FIG. 1 shows a system comprising devices for developing and executing one or more algorithms of a SaMD, according to a non-restrictive embodiment.

FIG. 1 shows a non-limiting example of a system 1 configured for the developing and the implementation of one or more SaMDs, or more generally of one or more health-related Apps, according to a non-restrictive embodiment.

The system 1 comprises a first computing device 10 and one or more second devices, for example 3 second devices 101, 102 and 103. The first and second devices may for example communicate via a network 100, e.g. using the Internet or the Cloud. The first device 10 is for example a desktop computer or a laptop computer or a server configured to develop the SaMD, i.e. to design, test and simulate the one or more algorithms comprised in the SaMD. The one or more algorithms may be for example made available to the second devices 101, 102 and 103 under the form of an application on dedicated digital distribution platform(s) such as for example Google Play and/or App Store by Apple. A second device corresponds for example to a desktop computer, a laptop, a smartphone, a tablet, a smart speaker such as Google Home or Amazon Echo. According to a variant, the SaMD is made available under the form of a web application, i.e. a client-server computer program that is run in a web browser on the second device(s). The first and/or second devices may be connected to the network 100 with wired connection such as Ethernet and/or with wireless connection such as Wifi® (IEEE 802.11x) or wireless connection compliant with standards compliant with the IMT-2000 specifications (also called 3G), with 3GPP LTE (also called 4G).

Figure 2:
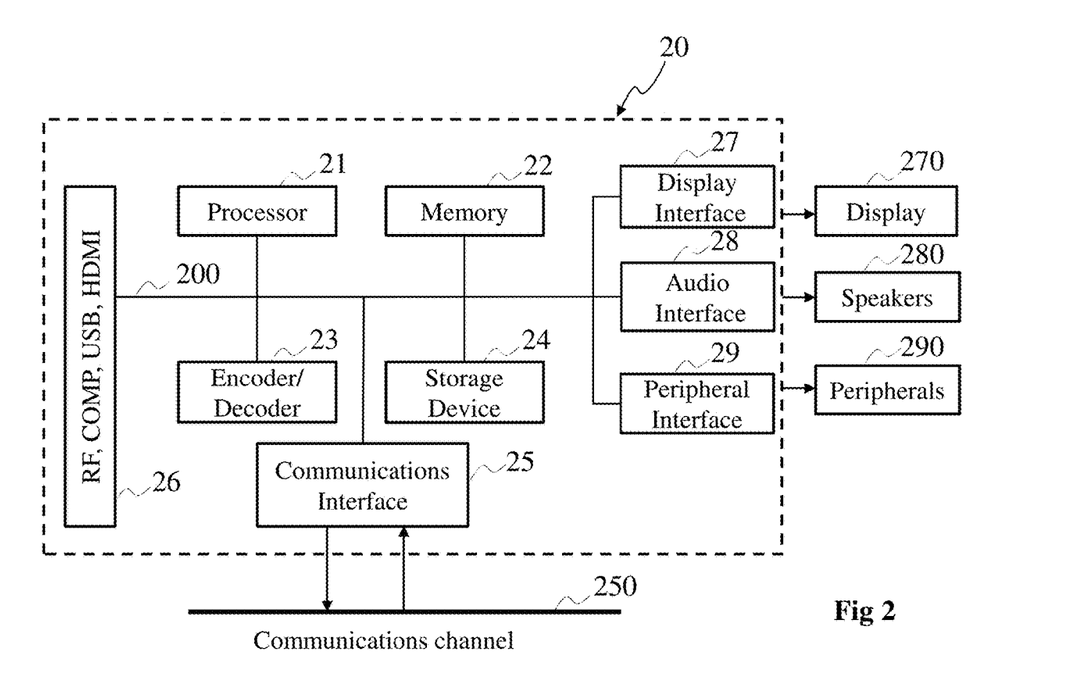
FIG. 2 shows an example architecture of a device of FIG. 1 which may be configured to implement a method or process described in relation with FIGS. 3, 4, 9 and/or 11, according to a non-restrictive embodiment.

FIG. 2 illustrates a block diagram of an example of a device or system in which various aspects and embodiments are implemented. The device 20 can be embodied as a device including the various components described below and is configured to perform one or more of the aspects described in this application. Examples of such devices include, but are not limited to, various electronic devices such as personal computers, laptop computers, smartphones, tablet computers, smart speakers, digital multimedia set top boxes, digital television receivers, personal video recording systems, connected home appliances, and servers. Elements of device 20, singly or in combination, can be embodied in a single integrated circuit, multiple ICs, and/or discrete components. For example, in at least one embodiment, the processing and encoder/decoder elements of device 20 are distributed across multiple ICs and/or discrete components. In various embodiments, the device is communicatively coupled to other similar systems, or to other electronic devices, via, for example, a communications bus or through dedicated input and/or output ports. In various embodiments, the device 20 is configured to implement one or more of the aspects described in this document. The system or device or apparatus 20 corresponds for example to the first device 10 and to each of the second devices 101, 102 and 103.

The device 20 includes at least one processor 21 (e.g., one or more CPUs and/or one or more GPUs) configured to execute instructions loaded therein for implementing, for example, the various aspects described in this document. Processor 21 can include embedded memory, input output interface, and various other circuitries as known in the art. The device 20 includes at least one memory 22 (e.g., a volatile memory device, and/or a non-volatile memory device). The device 20 includes a storage device 24, which can include non-volatile memory and/or volatile memory, including, but not limited to, EEPROM, ROM, PROM, RAM, DRAM, SRAM, flash, magnetic disk drive, and/or optical disk drive. The storage device 24 can include an internal storage device, an attached storage device, and/or a network accessible storage device, as non-limiting examples.

The device 20 may optionally include an encoder/decoder module 23 configured, for example, to process data to provide an encoded video or decoded video, and the encoder/decoder module 23 can include its own processor and memory. The encoder/decoder module 23 represents module(s) that can be included in a device to perform the encoding and/or decoding functions.

Program code to be loaded onto processor 21 or encoder/decoder 23 to perform the various aspects described in this document can be stored in storage device 24 and subsequently loaded onto memory 22 for execution by processor 21. In accordance with various embodiments, one or more of processor 21, memory 22, storage device 24, and encoder/decoder module 23 can store one or more of various items during the performance of the processes described in this document. Such stored items can include, but are not limited to, the stream of data representative of the one or more algorithms of the SaMD, matrices, variables, and intermediate or final results from the processing of equations, formulas, operations, and operational logic.

In several embodiments, memory inside of the processor 21 is used to store instructions and to provide working memory for processing that is needed during the executing of the one or more algorithms.

In other embodiments, however, a memory external to the processing device (for example, the processing device can be either the processor 21 or the encoder/decoder module 23) is used for one or more of these functions. The external memory can be the memory 22 and/or the storage device 24, for example, a dynamic volatile memory and/or a non-volatile flash memory. In several embodiments, an external non-volatile flash memory is used to store the operating system of a television. In at least one embodiment, a fast-external dynamic volatile memory such as a RAM is used as working memory.

The input to the elements of device 20 can be provided through various input devices as indicated in block 26. Such input devices include, but are not limited to, (i) an RF portion that receives an RF signal transmitted, for example, over the air by a broadcaster, (ii) a Composite input terminal, (iii) a USB input terminal, and/or (iv) an HDMI input terminal.

In various embodiments, the input devices of block 26 have associated respective input processing elements as known in the art. For example, the RF portion can be associated with elements necessary for (i) selecting a desired frequency (also referred to as selecting a signal, or band-limiting a signal to a band of frequencies), (ii) down-converting the selected signal, (iii) band-limiting again to a narrower band of frequencies to select (for example) a signal frequency band which can be referred to as a channel in certain embodiments, (iv) demodulating the down-converted and band-limited signal, (v) performing error correction, and (vi) demultiplexing to select the desired stream of data packets. The RF portion of various embodiments includes one or more elements to perform these functions, for example, frequency selectors, signal selectors, band-limiters, channel selectors, filters, downconverters, demodulators, error correctors, and demultiplexers. The RF portion can include a tuner that performs various of these functions, including, for example, down-converting the received signal to a lower frequency (for example, an intermediate frequency or a near-baseband frequency) or to baseband.

In one set-top box embodiment, the RF portion and its associated input processing element receives an RF signal transmitted over a wired (for example, cable) medium, and performs frequency selection by filtering, down-converting, and filtering again to a desired frequency band.

Various embodiments rearrange the order of the above-described (and other) elements, remove some of these elements, and/or add other elements performing similar or different functions.

Adding elements can include inserting elements in between existing elements, such as, for example, inserting amplifiers and an analog-to-digital converter. In various embodiments, the RF portion includes an antenna.

Additionally, the USB and/or HDMI terminals can include respective interface processors for connecting device 20 to other electronic devices across USB and/or HDMI connections. It is to be understood that various aspects of input processing, for example, Reed-Solomon error correction, can be implemented, for example, within a separate input processing IC or within processor 21 as necessary. Similarly, aspects of USB or HDMI interface processing can be implemented within separate interface ICs or within processor 21 as necessary. The demodulated, error corrected, and demultiplexed stream is provided to various processing elements, including, for example, processor 21, and encoder/decoder 1230 operating in combination with the memory and storage elements to process the data stream as necessary for presentation on an output device.

Various elements of device 20 can be provided within an integrated housing. Within the integrated housing, the various elements can be interconnected and transmit data therebetween using suitable connection arrangement, for example, an internal bus as known in the art, including the I2C bus, wiring, and printed circuit boards.

The device 20 includes communication interface 25 that enables communication with other devices via communication channel 250. The communication interface 25 can include, but is not limited to, a transceiver configured to transmit and to receive data over communication channel 250. The communication interface 25 can include, but is not limited to, a modem or network card and the communication channel 250 can be implemented, for example, within a wired and/or a wireless medium. The device can output stream(s) of data (e.g. the stream(s) of data representative of the one or more algorithms of the SaMD) and signal including such stream(s) via communication channel 250 using the communication interface 25.

Data is streamed to the device 20, in various embodiments, using a Wi-Fi network such as IEEE 802.11. The Wi-Fi signal of these embodiments is received over the communications channel 250 and the communications interface 25 which are adapted for Wi-Fi communications. The communications channel 250 of these embodiments is typically connected to an access point or router that provides access to outside networks including the Internet for allowing streaming applications and other over-the-top communications.

Other embodiments provide streamed data to the device 20 using a set-top box that delivers the data over the HDMI connection of the input block 26.

Still other embodiments provide streamed data to the device 20 using the RF connection of the input block 26.

The device 20 can provide an output signal to various output devices, including a display 270, speakers 280, and/or other peripheral devices 290. The other peripheral devices 290 include, in various examples of embodiments, one or more of a stand-alone DVR, a disk player, a stereo system, a lighting system, and other devices that provide a function based on the output of the device 20.

In various embodiments, control signals are communicated between the device 20 and the display 270, speakers 280, or other peripheral devices 290 using signaling such as AV.Link, CEC, or other communications protocols that enable device-to-device control with or without user intervention.

The output devices can be communicatively coupled to device 20 via dedicated connections through respective interfaces 27, 28, and 29.

Alternatively, the output devices can be connected to device 20 using the communications channel 250 via the communications interface 25. The display 270 and speakers 280 can be integrated in a single unit with the other components of device 20 in an electronic device such as, for example, a television, a smartphone, a tablet.

In various embodiments, the display interface 27 includes a display driver, such as, for example, a timing controller (T Con) chip.

The display 270 and speaker 280 can alternatively be separate from one or more of the other components, for example, if the RF portion of input 26 is part of a separate set-top box. In various embodiments in which the display 270 and speakers 280 are external components, the output signal can be provided via dedicated output connections, including, for example, HDMI ports, USB ports, or COMP outputs.

Figure 3:
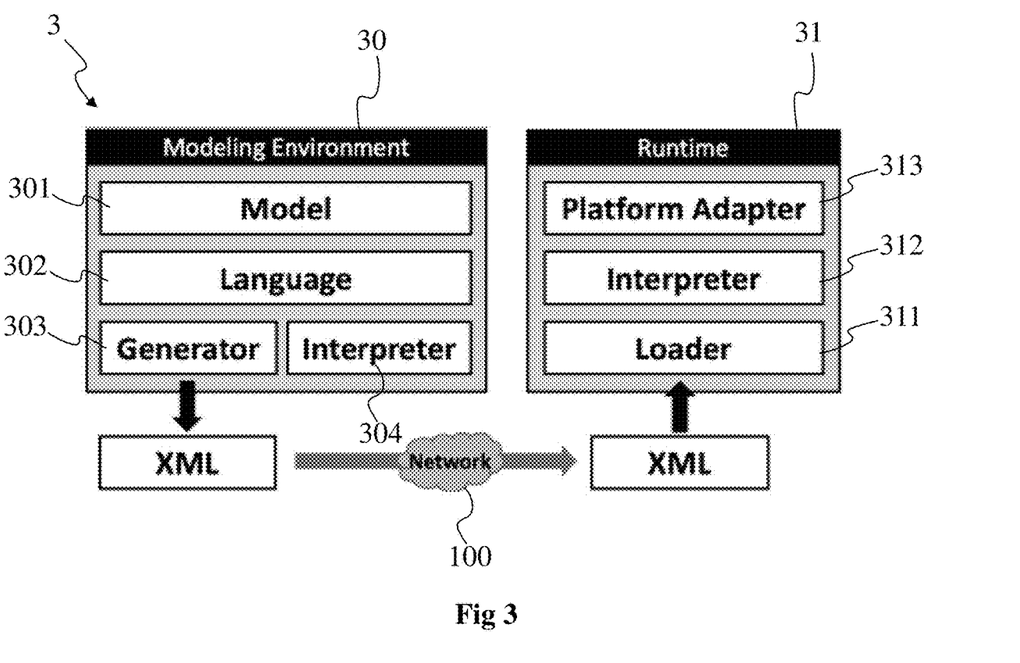
FIG. 3 shows an overview of the architecture of the system of FIG. 1, according to a non-restrictive embodiment.

FIG. 3 illustrates a general overview of the architecture of a system 3 configured for developing a SaMD and implementing it, according to a non-restrictive embodiment.

The system 3 comprises for example a first environment 30 configured for the modelling of the one or more algorithms comprised in the SaMD and a second environment 31 configured for executing the one or more algorithms. The first environment 30 may for example be implemented in the first device 10 and the second environment 31 may for example implemented in one of the second devices 101 to 103, or in each one of the second devices 101 to 103.

The first environment 30 and the second environment 31 each comprises so-called modules, which may be implemented under the form of hardware, software or a combination of hardware and software. The modules may also be understood as functional modules implementing operations to perform a process, for example developing algorithms of a SaMD and/or executing these algorithms at runtime.

The first environment 30 may be used by mixed teams of medical/technical professionals to design the algorithms underlying the SaMD. They rely on the determined DSL built specifically for the medical area, which provide abstractions and notations meaningful to HCPs. These include decision tables, decision trees and numbers with ranges, but also state machines to capture the asynchronous, event-based, time-sensitive execution of the algorithms. Additional languages support is available for defining tests and simulation scenarios as well as for specifying various configuration options for visualizations and simulations. The determined DSL may include first, second and third programming language items, also called concepts, that may be used for the designing, simulating and testing of the algorithms. The number of concepts of the determined DSL is limited in comparison to the number of concepts of GPL for example. For example, the number of concepts of the determined DSL is equal to 200, 250, 300 or 400 while the number of concepts of GPL might be equal to 1500 or more. Concepts include for example expressions, state machines, testing functions or scenarios, configuration models.

The first environment 30 corresponds advantageously to a LWB environment, for example Jetbrains MPS, which comprises a model module 301, a language module 302, a generator 303 and an interpreter 304. The first, second and third set of concepts of the DSL are built with MPS, and the modeling environment 30 is a stripped-down version of MPS as well. The first environment comprises a model module 301 allowing to create an algorithm based on a language module 302. The model module 301 can leverage the projectional editor and the DSL languages imported. The language module 302 allows to create DSL by defining its concepts, concept constraints, language aspects (how they are projected to the user in the projectional editor, structure, behavior, intentions, etc). The first environment 30 comes with an interpreter 304 that is able to run the algorithms for simulation and testing directly in the modeling environment. The generator 303 is adapter to generate a stream of data representative of the algorithms of the SaMD that is easily interpretable at runtime. The stream of data may for example take the form of XML (Extensible Markup Language) files that may be send to end-user device(s) such as the second devices 101 to 103 via the network 100. The format of the output stream(s) of data is not limited to XML and may be according to variants JSON (JavaScript Object Notation) or binary as well.

The second environment 31 corresponds to a runtime environment (RTE) that may be embedded in a mobile and/or web application running on an end-user device. The runtime environment embedded in the mobile applications contains a loader 311 to load the one or more algorithms of the SaMD and an interpreter 312 (different from the interpreter 304), for example written in C++, which, after separate compilation, runs both on Android and iOS platforms. The interpreter 312 consumes the algorithms in the form of XML files created by the generator 303 and loaded over the network 100 to the user' devices. Platform-specific libraries and frameworks 313 are used for integration with the two platforms, for example, for accessing sensors and system values, storing data and User Interface.

Figure 4:
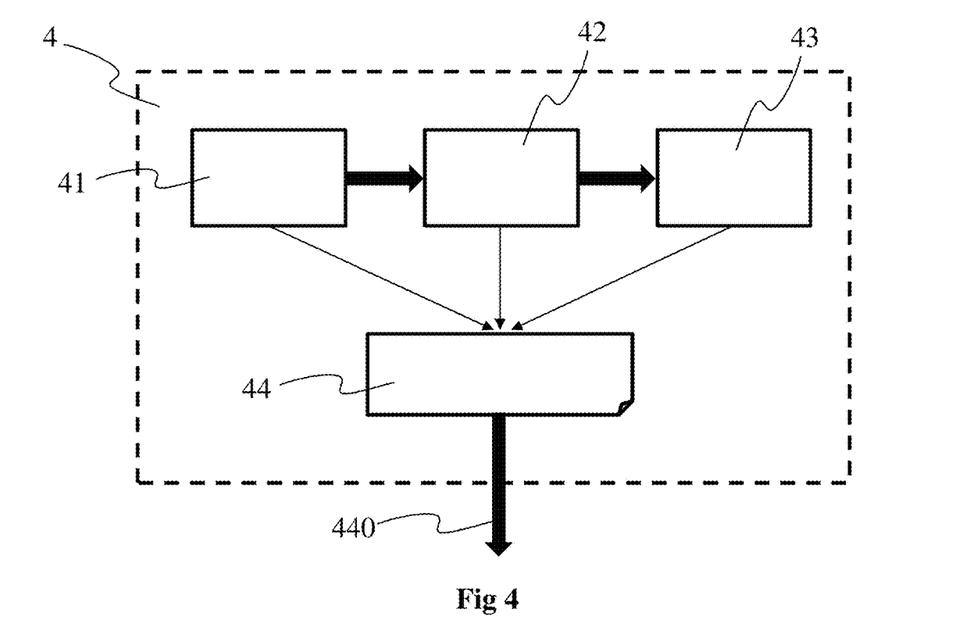
FIG. 4 shows an example of an environment used to design and/or develop at least an algorithm of a SaMD, according to a non-restrictive embodiment.

FIG. 4 illustrates an exemplary functional overview of the architecture of an Integrated Development Environment (IDE) 4 corresponding to the first environment 30, according to a non-restrictive embodiment.

The IDE 4 is configured for the designing/modelling of the one or more algorithms comprised in the SaMD. The IDE 4 may for example be implemented in the first device 10 and/or device 20.

The IDE 4 comprises so-called modules, which may be Implemented under the form of hardware, software or a combination of hardware and software. The modules may also be understood as functional modules implementing operations to perform a process, i.e. developing algorithms of a SaMD. The IDE corresponds to a LWB tool/environment.

The IDE 4 comprises 3 modules, namely a first module 41 configured/adapted to design the one or more algorithms, a second module 42 configured/adapted to simulate the one or more algorithms and a third module 43 configured/adapted to test the one or more algorithms. The 3 modules 41 to 43 each run on the same platform/environment, namely a LWB platform/environment, for example on Jetbrains MPS. The 3 modules 41 to 43 each participate in the design/modelling/ developing of the one or more algorithms 44 forming parts of the medical software.

The first module 41 uses a first set of concepts of the determined DSL to design the one or more algorithms. The first module 41 allows for example to create the main state machine of each algorithm with associated items (decision trees and tables, functions, medical types). An algorithm may comprise for example questions to patients, events for prompting patient answers, questionnaires, notifications, messages for medical recommendations, time management, etc. The design of the one or more algorithms may also be constrained to a Finite State Automaton model, enforcing Algorithm Developer (also known as Software Specialist) to organize and lay out the one or more algorithms in a specific way following best practices, as opposed to GPL, with which no best structure for creating the one or more algorithms is enforced. The first module is further adapted to automatically generate medical protocol(s) or decision tree(s) of each of the algorithm, enabling medical experts to review and validate the algorithm. Indeed, the use of concepts of a DSL designed for medical or health domain renders the protocol easily interpretable and understandable by non-software specialists.

Figure 5:
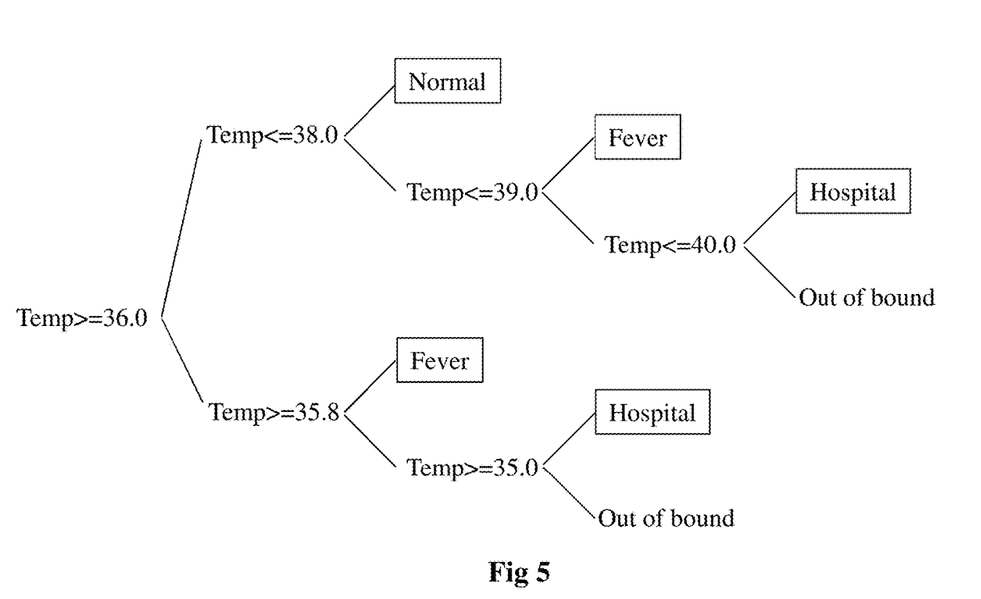
FIG. 5 shows a graphical representation of a decision tree of the algorithm obtained with the environment of FIG. 4, according to a non-restrictive embodiment.

FIG. 5 illustrates an example of a decision tree that may be automatically generated. The example of FIG. 5 corresponds to a decision tree for establishing a recommendation or a diagnosis according to the temperature of a person using the medical application/SaMD.

Figure 8:
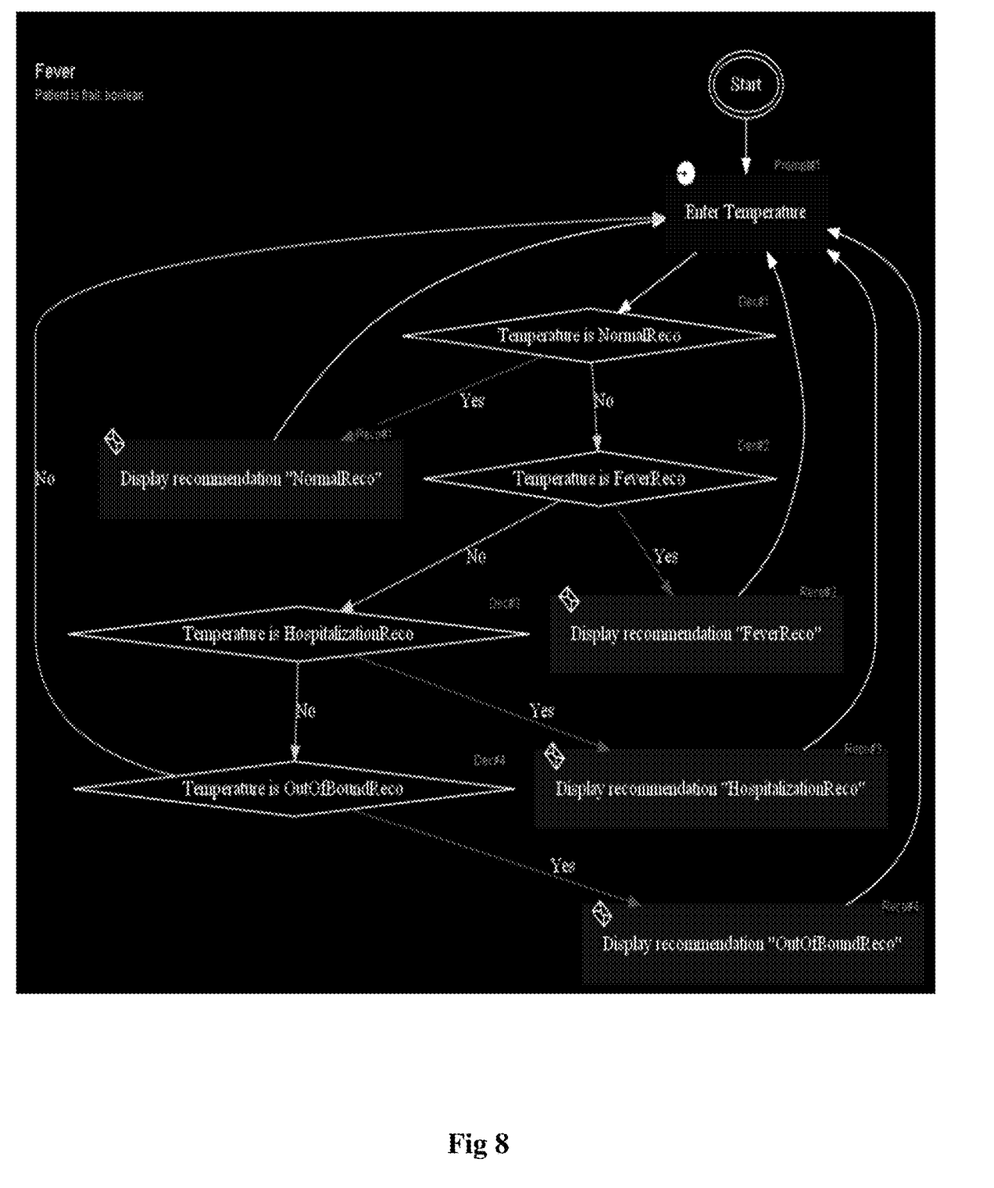
FIG. 8 shows an example of a medical protocol generated from an algorithm of the SaMD and obtained with the environment of FIG. 4, according to a non-restrictive embodiment.

FIG. 8 illustrates an example of a medical protocol that may be automatically generated. The example of FIG. 8 corresponds to a medical protocol associated with the decision tree of FIG. 5 for establishing a recommendation or a diagnosis according to the temperature of a person using the medical application/SaMD.

An example of a state machine is as follows (fever state machine):

| State machine FeverStateMachine | |
| --- | --- |
| inputs: | frailty :boolean |
| outputs: | <<...>> |
| messages: | |
| MessageAskTemperature(message:valuedEnumType<FeverRequest>) | |
| MessageAppRecommendation(reco:valuedEnumType<FeverReco>) | |
| events in: | Event_TakeTemperature(temperature:real) |
| events out: | <<...>> |
| tags declarations: | #background #request |
| show work item | ☒ |
| show tags | ☒ |
| variables: temp:valuedEnumType<FeverReco> | |
| global transitions: <<...>> | |
| start: State CheckTemperature | |
| (State_CheckTemperature) state | |
| Entry: #background | |
|    sendMesssage MessageAskTemperature(Req_Temp) | |
| exit: <<...>> | |
| links: on Event_TakeTemperature with #background | |
|    temp =  CheckFeverDecisionTree(frailty,temperature) | |
|    [temp = Normal] → State_Normal | |
|    [temp = Fever] → State_Fever | |
|    [temp = Hospitalization] → State_Hospitalization | |
|    [temp = Out of bound] → State_OutOfBound | |
| (State_Normal) state | |
| entry: sendMessage MessageAppRecommendation(Normal) | |
| exit: <<...>> | |
| links: #background | |
|    on epsilon [<no guard>] → State CheckTemperature | |

-continued

| (State_Fever) state |
| --- |
| entry: sendMessage MessageAppRecommendation(Fever)<br>exit: <<...>><br>links: #background<br>    on epsilon [<no guard>] → State CheckTemperature |

| (State_Hospitalization) state |
| --- |
| entry: sendMessage MessageAppRecommendation(Hospitalization)<br>exit: <<...>><br>links: #background<br>    on epsilon [<no guard>] → State CheckTemperature |

| (State_OutOfBound) state |
| --- |
| entry: sendMessage MessageAppRecommendation(Out of Bound)<br>exit: <<...>><br>links: #background<br>    on epsilon [<no guard>] → State CheckTemperature |

Examples of types for the state machine are as follows:
Type Definitions FeverTypes
type FeverTemp: number [30][42]{1}
enum FeverMode {Oral, Tympanic}
enum FeverAppContent<String>{
    takeTemp →"Please give me your temperature in celsius">
    takeSymptoms →"Do you have any of the following symptoms"
}
enum FeverRecos<string>{
    RecoNormal →"Your temperature is normal, hurray! Report it to me when you feel hot or cold."
    RecoTakeMedicine →
    "Your temperature is high, you need to take a paracetamol. Please recheck your temperature in 6 hours."
    RecoCallCareTeam →"Call your care team now. "
    RecoRecheckInTen →"Recheck your temperature in ten minutes."
    RecoTakeSomethingWarm →"Your temperature is low, have something warm and recheck your temperature in 6 hours."
}
Enum FeverNotification<String>{
    feverNotify →"It's time to recheck your temperature."
}

Figure 6:
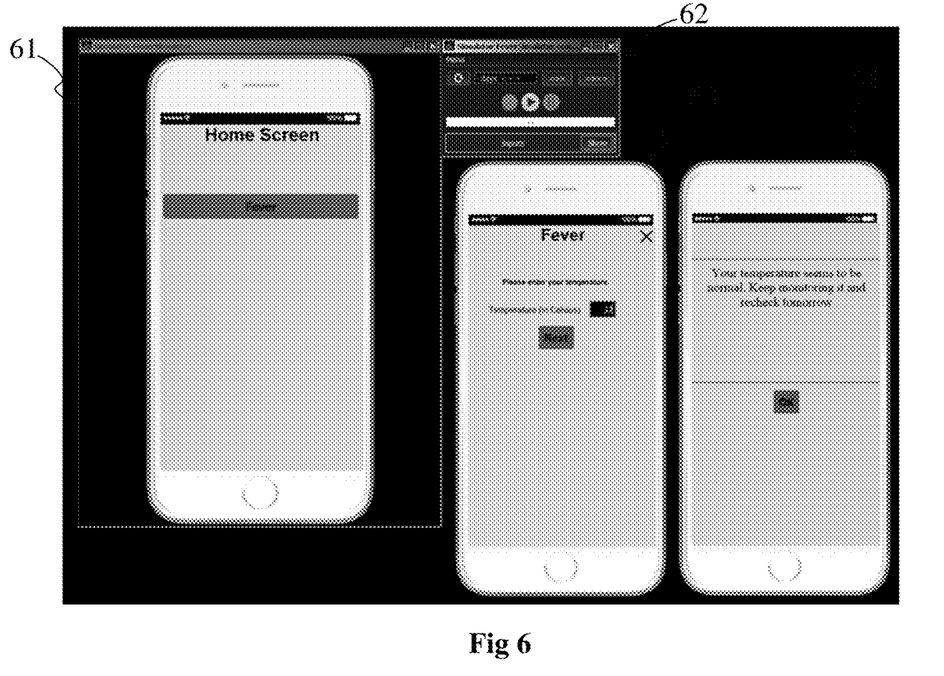
FIG. 6 shows a graphical representation of the simulation of an algorithm of a SaMD obtained with the environment of FIG. 4, according to a non-restrictive embodiment.
Figure 7:
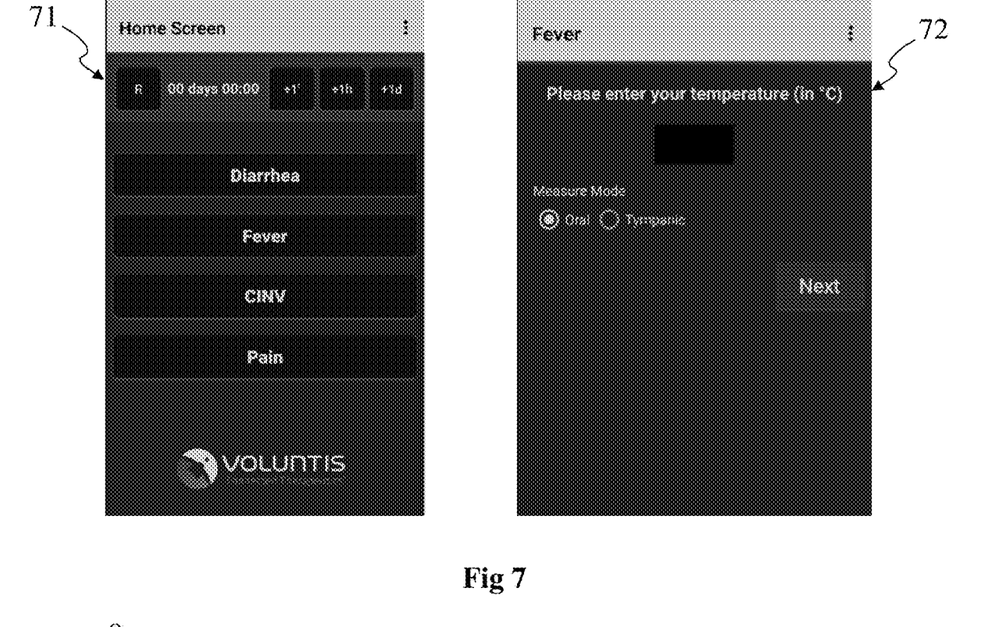
FIG. 7 shows graphical representations of user interface obtained when executing the SaMD on an end-user device, according to a non-restrictive embodiment.

The second module 42 uses a second set of concepts of the determined DSL to generate a simulation of the one or more algorithms, for example a graphical representation for graphical interface (as displayed on smartphones or tablets for example) or a sound representation for sound interface (such as a smart speaker). The second module 42 allows to define the texts that will be displayed and/or rendered to the user, and to use a mock-up of a mobile application and/or web application. The second module enables to simulate the behavior of the one or more algorithm directly in the IDE 4, without waiting that the whole process of software design is finished to test the software at runtime. The second module 42 enables to evaluate the medical relevance and to review the one or more algorithms right away, without all delays incurred by classical approaches (implementation of the medical algorithms on all the target architectures), thus allowing quick and iterative creation by constant interaction between Medical Specialists and Software Specialists with a common understanding of the one or more algorithms currently designed. FIG. 6 illustrates examples of graphical representations 61, 62, 63 and 64 of some interfaces that are generated to ask questions to a user and receive answers/inputs from the user, as it would be on the end-user device running the SaMD at runtime. The example of FIG. 6 the based on an application running on a smartphone. Graphical layout may be configurable but may be mostly targeted to a smartphone-like layout, so that the user can experience how the patient user would use the one or more algorithms of the SaMD. User can also simulate time management in the medical algorithms (e.g., see how the mobile app would trigger notification/reminder to recheck her medical condition after 24 hours). Validation of the algorithm is simplified by using the DSL. The decision trees and decision tables are suitable for review directly by non-software experts, for example HCPs. The second module 42, i.e. a simulator, makes use of the interpreter 304 to let non-software specialists simulate the behavior of the models, resembling the interaction with the algorithm on the end-user device. Specific executions of the simulator can be recorded into test cases for automatic re-execution and detection of regression errors.

The third module 43 uses a third set of concepts of the determined DSL to generate test functions and/or use scenarios for testing the one or more algorithms, enabling the user and/or HCPs to ensure that the results are conforming to the medical expectations. The third module 43 allows to test functions and decision trees/tables, to test the overall logic of a medical algorithm through scenarios, and evaluate the coverage of the tests and scenarios, i.e. what is the amount of the one or more algorithm covered by tests. The result of a test can be PASS (does work as expected) or FAIL (does not work as expected). The third module 43 allows to check and visualize which parts of the medical algorithms are covered by tests and which are not, enabling to quickly ensure a 100% coverage of the one or more algorithms.

Example of a test function is as follows:

FeverScenarios : scenarios for FeverStatMachine [Run all] [Abort]
passed 11
failed 0
not run 0
started at 22/10/2018 23:15:32 CEST , elapsed time: 00h 00m 00s
PASS
simulation step is of 60 seconds
scenario scenario_1
    global timeout: 1 day
    time granularity: 60 seconds
given
    <<...>>
when
    at 0 hours: eventInTakeTemperature(answers to FeverTakeTemperatureQuestionnaire { )
                              temp: 39
                              mode: oral
                              }
    at 1 hours: eventInAskReInitialize( )
then
    at 59 min: assert parent event eventInSymptoms is handled
    at 1 hours; assert message for eventInTakeTemperature is MessageAppContent(takeTemp)
[Simulate]    ☒ Show rewind panel The first, second and third modules 41 to 43 interact with each other in the design/modelling/developing of the one or more algorithms 44 forming parts of the medical software. The one or more algorithms are then generated 440 under the form of one or more streams of data, for example in XML format.

Figure 9:
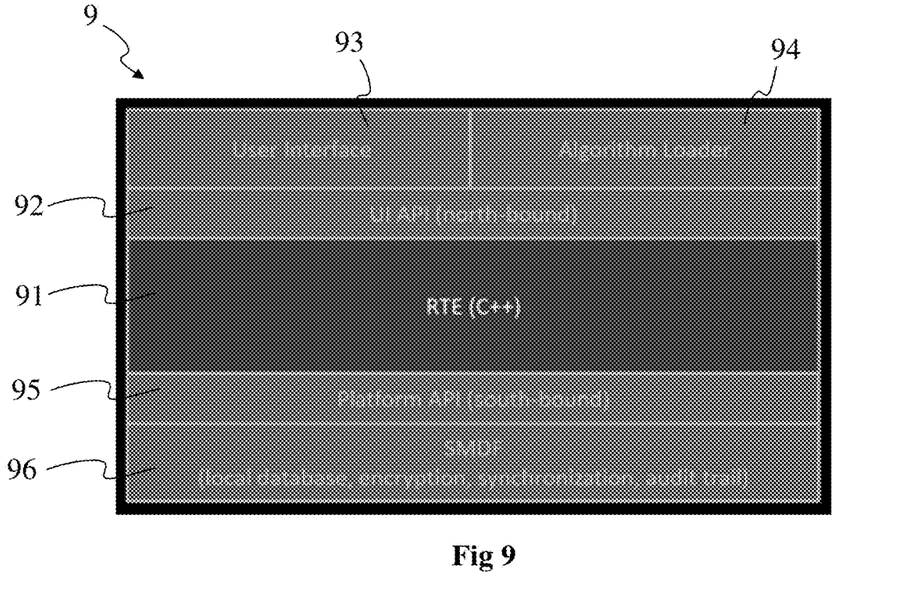
FIG. 9 shows an overview of an architecture of a logical system configured to execute the SaMD on an end-user device of FIG. 1, according to a non-restrictive embodiment.

FIG. 9 illustrates an exemplary functional overview of an application with an embedded Run-Time Environment (RTE) corresponding to the second environment 31, according to a non-restrictive embodiment.

The north-bound layer 92 may connect the RTE 91 with the User interface 93 and the algorithm loader 94 in charge of the management of the one or more algorithms received for example under the form of XML files. The south-bound layer 95 (also called platform API) may connect the RTE 91 with the underlying components 95 of the application (Software Medical Device Framework) for data persistence, data encryption, data synchronization with web/mobile, etc The RTE 91 may correspond to an interpreter that takes the XML algorithms and interface the algorithms with the external environment (mobile, web interface, etc.). The RTE 91 may encapsulates the medical logic from the algorithm and is portable to any technical architecture supporting C++ (PC, Mac, Android Smartphones/tablets, iOS smartphones/tablets, etc.). In other words, the RTE 91 is aimed at being embedded in target device apps to interpret and process the medical algorithms in XML, based on user inputs and time. The RTE 91 is portable to any third-party architecture able to compile C++.

The opportunity to export the one or more algorithms and use them on target architectures which embed the RTE 91 allow to "code once, work everywhere", thus saving time (no multiple developments with multiple GPLs), efforts (each GPL require a specific Software Specialist), and diminishing implementation errors/risks (medical algorithms, by the mean of the RTE, behave exactly the same as on the IDE 4).

Figure 10:
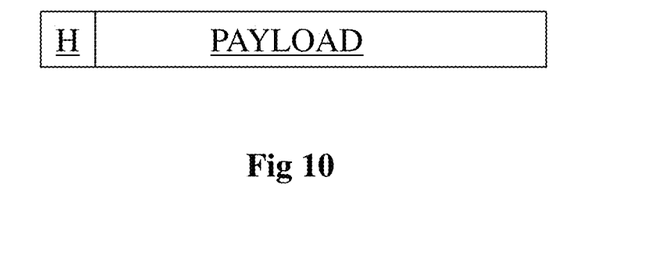
FIG. 10 shows an example of a syntax of a signal transporting a stream of data obtained with the method and/or process of FIGS. 4 and/or 11, according to a non-restrictive embodiment.

FIG. 10 shows an embodiment of the syntax of a signal transmitted for example between the first device 10 and one or more second devices 101 to 103 when the data are transmitted over a packet-based transmission protocol. Each transmitted packet P comprises a header H and payload data PAYLOAD. The Payload comprises for example the data representative of the one or more algorithms of the SaMD, for example in the XML format.

Figure 11:
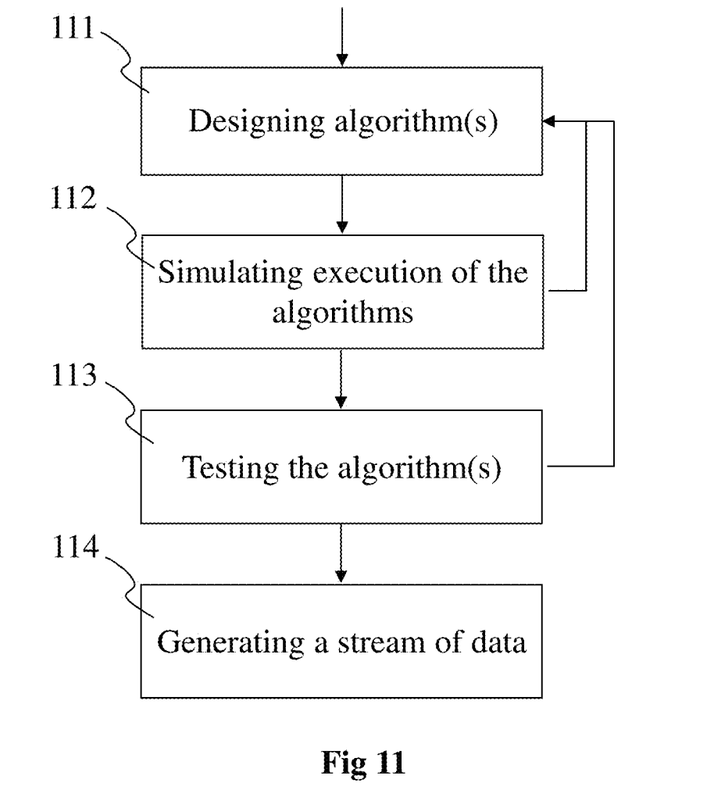
FIG. 11 shows an example of a method for generating a stream of data representative of at least an algorithm of a SaMD, implemented for example in the device of FIG. 2, according to a non-restrictive embodiment.

FIG. 11 illustrates a method for generating a stream of data, the data being representative of at least an algorithm of a software as a medical device, according to a non-restrictive embodiment. The method may for example be implemented in the device 10 and/or 20. The different parameters of the device 20 may be updated.

In a first operation 111, the at least an algorithm is designed using first programming language items/concepts of a determined domain-specific language, i.e. a DSL language designed for the medical or health domain. The determined DSL is obtained/designed using a determined language workbench environment, for example Jetbrains MPS.

In a second operation 112, an executing of the at least an algorithm is simulated with a simulation environment (also called simulator) that is obtained by using second programming language items/concepts of the determined DSL. The simulating is implemented in the determined language workbench environment, i.e. in the same environment than the designing of the one or more algorithm at operation 111.

In a third operation 113, the at least an algorithm is tested with at least a test function written with third programming language items/concepts of the determined DSL. The testing, like the designing and the simulating, is implemented in the same determined language workbench environment.

In a fourth operation 114, the stream of data representative of the at least an algorithm is generated, for example in the XML format, as a result of the preceding operation(s). According to an optional variant, the stream may be generated according to the result of the testing and/or simulating.

For example, if the testing and/or simulating results conform the requirements, the stream of data is generated. Otherwise, the one or more algorithms may be redesigned, at least in part, to correct for any detected errors before being tested and simulated again.

According to a specific embodiment, the at least an algorithm is designed according to a model of a finite state automaton.

According to a further embodiment, the method further comprises automatically generating a graphical representation of at least a medical protocol from the at least an algorithm in the determined language workbench environment.

According to another embodiment, the method further comprises interpreting and processing the stream of data in a run-time environment embedded in at least a target application.

According to a particular embodiment, the at least a target application is configured to be executed on a determined target architecture among a plurality of target architectures, e.g. Android and/or iOS, the run-time environment being identical for each and every target architecture of the plurality.

Naturally, the present document is not limited to the embodiments previously described.

In particular, the present document is not limited to a method and device for generating a stream of data but also extends to a method for transmitting such a stream of data and/or a method for receiving such a stream of data to interpret and process it in a RTE in an end-user device and to any device implementing these methods and notably any devices comprising at least one CPU and/or at least one GPU.

The implementations described herein may be implemented in, for example, a method or a process, an apparatus, a computer program product, a data stream, or a signal. Even if only discussed in the context of a single form of implementation (for example, discussed only as a method or a device), the implementation of features discussed may also be implemented in other forms (for example a program). An apparatus may be implemented in, for example, appropriate hardware, software, and firmware. The methods may be Implemented in, for example, an apparatus such as, for example, a processor, which refers to processing devices in general, including, for example, a computer, a microprocessor, an integrated circuit, or a programmable logic device. Processors also include communication devices, such as, for example, Smartphones, tablets, computers, mobile phones, portable/personal digital assistants ("PDAs"), and other devices that facilitate communication of information between end-users.

Implementations of the various processes and features described herein may be embodied in a variety of different equipment or applications, particularly, for example, equipment or applications associated with data encoding, data decoding, view generation, texture processing, and other processing of images and related texture information and/or depth information. Examples of such equipment include an encoder, a decoder, a post-processor processing output from a decoder, a pre-processor providing input to an encoder, a video coder, a video decoder, a video codec, a web server, a set-top box, a laptop, a personal computer, a cell phone, a PDA, and other communication devices. As should be clear, the equipment may be mobile and even installed in a mobile vehicle.

Additionally, the methods may be implemented by instructions being performed by a processor, and such instructions (and/or data values produced by an implementation) may be stored on a processor-readable medium such as, for example, an integrated circuit, a software carrier or other storage device such as, for example, a hard disk, a compact diskette ("CD"), an optical disc (such as, for example, a DVD, often referred to as a digital versatile disc or a digital video disc), a random access memory ("RAM"), or a read-only memory ("ROM"). The instructions may form an application program tangibly embodied on a processor-readable medium. Instructions may be, for example, in hardware, firmware, software, or a combination. Instructions may be found in, for example, an operating system, a separate application, or a combination of the two. A processor may be characterized, therefore, as, for example, both a device configured to carry out a process and a device that includes a processor-readable medium (such as a storage device) having instructions for carrying out a process. Further, a processor-readable medium may store, in addition to or in lieu of instructions, data values produced by an implementation.

As will be evident to one of skill in the art, implementations may produce a variety of signals formatted to carry information that may be, for example, stored or transmitted. The information may include, for example, instructions for performing a method, or data produced by one of the described implementations. For example, a signal may be formatted to carry as data the rules for writing or reading the syntax of a described embodiment, or to carry as data the actual syntax-values written by a described embodiment. Such a signal may be formatted, for example, as an electromagnetic wave (for example, using a radio frequency portion of spectrum) or as a baseband signal. The formatting may include, for example, encoding a data stream and modulating a carrier with the encoded data stream. The information that the signal carries may be, for example, analog or digital information. The signal may be transmitted over a variety of different wired or wireless links, as is known. The signal may be stored on a processor-readable medium.

A number of implementations have been described. Nevertheless, it will be understood that various modifications may be made. For example, elements of different implementations may be combined, supplemented, modified, or removed to produce other implementations. Additionally, one of ordinary skill will understand that other structures and processes may be substituted for those disclosed and the resulting implementations will perform at least substantially the same function(s), in at least substantially the same way(s), to achieve at least substantially the same result(s) as the implementations disclosed. Accordingly, these and other implementations are contemplated by this application.

The invention claimed is:

1. A method of generating a stream of data, said data being representative of at least an algorithm of a software as a medical device, the method comprising:
designing said at least an algorithm using first programming language items of a determined domain-specific language, said determined domain-specific language being obtained using a determined language workbench environment;
simulating an executing of said at least an algorithm with a simulation environment obtained using second programming language items of said determined domain-specific language, said simulating being implemented in said determined language workbench environment;
testing said at least an algorithm with at least a test function written with third programming language items of said determined domain-specific language, said testing being implemented in said determined language workbench environment;
generating said stream of data.

2. The method according to claim 1, wherein said at least an algorithm is designed according to a model of a finite state automaton.

3. The method according to claim 1, further comprising automatically generating a graphical representation of at least a medical protocol from said at least an algorithm in said determined language workbench environment.

4. The method according to claim 1, further comprising interpreting and processing said stream of data in a run-time environment embedded in at least a target application.

5. The method according to claim 4, wherein said at least a target application is configured to be executed on a determined target architecture among a plurality of target architectures, said run-time environment being identical for any target architecture of said plurality.

6. A device configured for generating a stream of data, said data being representative of at least an algorithm of a software as a medical device, the device comprising a memory associated with at least a processor configured for:
designing said at least an algorithm using first programming language items of a determined domain-specific language, said determined domain-specific language being obtained using a determined language workbench environment;
simulating an executing of said at least an algorithm with a simulation environment obtained using second programming language items of said determined domain-specific language, said simulating being implemented in said determined language workbench environment;
testing said at least an algorithm with at least a test function written with third programming language items of said determined domain-specific language, said testing being implemented in said determined language workbench environment;
generating said stream of data.

7. The device according to claim 6, wherein said at least an algorithm is designed according to a model of a finite state automaton.

8. The device according to claim 6, wherein said at least a processor is further configured for automatically generating a graphical representation of at least a medical protocol from said at least an algorithm in said determined language workbench environment.

9. A system comprising the device according to claim 6, and an apparatus comprising a memory associated with at least a processor configured for interpreting and processing said stream of data in a run-time environment embedded in at least a target application.

10. The system according to claim 9, wherein said at least a target application is configured to be executed on a determined target architecture of said apparatus among a plurality of target architectures, said run-time environment being identical for any target architecture of said plurality.

11. A computer program product comprising program code instructions stored in a non-transitory processor readable medium to execute the method according to claim 1, when this program is executed on a computer.

12. A non-transitory processor readable medium having stored therein instructions for causing a processor to perform the method according to claim 1.

* * * * *